United States Patent [19]

Chambers et al.

[11] Patent Number: 5,219,860
[45] Date of Patent: Jun. 15, 1993

[54] SPIROCYCLIC ANTIPSYCHOTIC AGENTS

[75] Inventors: Mark S. Chambers, Watford, England; David C. Billington, Lavallois Perret, France

[73] Assignee: Merck Sharp & Dohme Limited, Hoddesdon, England

[21] Appl. No.: 662,602

[22] Filed: Mar. 1, 1991

[30] Foreign Application Priority Data

Mar. 5, 1990 [GB] United Kingdom ............... 9004900
Nov. 22, 1990 [GB] United Kingdom ............... 9025385

[51] Int. Cl.$^5$ .................... C07D 221/20; A61K 31/44
[52] U.S. Cl. ........................................ 514/278; 546/17
[58] Field of Search ........................... 546/17; 514/278

[56] References Cited

U.S. PATENT DOCUMENTS 3,125,580  3/1964  Janssen ..................... 546/17

FOREIGN PATENT DOCUMENTS 0431943  6/1991  European Pat. Off. ............. 546/17

OTHER PUBLICATIONS

Reimann et al "Synthese von 3,4-dihydro . . . " Arch. Pharm. 320(5) 385-393 (1987).
Reimann et al "Synthese und pharmakcologische . . . " Arch. Pharm. 323(1) 35-39 (1990) (Jan. 1990).
Hashigaki et al "Synthesis and structure . . . " Chem. Pharm. Bull 32(9) 3561-8 (1984).
Hackh "Chemical Dictionary" p. 331, 1983.

Primary Examiner—C. Warren Ivy
Assistant Examiner—Celia Chang
Attorney, Agent, or Firm—Robert J. North; Joseph F. DiPrima

[57] ABSTRACT

A class of spirocyclic piperidine derivatives are selective ligands at sigma recognition sites and are therefore useful in the treatment and/or prevention of psychiatric disorders.

5 Claims, No Drawings

SPIROCYCLIC ANTIPSYCHOTIC AGENTS

This invention relates to a class of spirocyclic piperidine derivatives which are selective ligands at sigma recognition sites and are therefore useful as neuroleptic agents.

Various spirocyclic piperidine derivatives are already known. For example, JP-A-55-143980 generically discloses inter alia a class of spiro[indane-1,4'-piperidine] derivatives which are substituted on the ring nitrogen atom by hydrogen or by one of a range of hydrocarbon substituents. There is, however, no specific disclosure therein of a compound possessing a spiro[indane-1,4'-piperidine] ring system. The compounds described in JP-A-55-143980 are stated to exhibit antiallergic activity. No suggestion is made in JP-A-55-143980 that the compounds described therein may be of any assistance in solving the problem of providing an effective agent for the treatment and/or prevention of psychiatric disorders.

U.S. Pat. No. 3,125,580 describes inter alia a class of spiro[indane-1,4'-piperidine] derivatives. These compounds are variously N-substituted by a 3-cyano-3,3diphenylpropyl or 3-alkanoyl-3,3-diphenylpropyl group. Unsubstituted, N-cyano-substituted and N-benzyl-substituted spiro[indane-1,4'-piperidine] derivatives are also disclosed as intermediates. The compounds described in U.S. Pat. No. 3,125,580 are stated to be potent analgesics with a relatively long duration of activity, and to possess mydriatic activity. There is no suggestion in U.S. Pat. No. 3,125,580 that the compounds disclosed therein may be of any use as neuroleptic agents.

Most of the numerous currently available clinically effective antipsychotic drugs are dopamine $D_2$ receptor antagonists. As a result, they produce a characteristic spectrum of undesirable side-effects. These include endocrine effects and extrapyramidal side-effects, as well as often irreversible tardive dyskinesia. In addition, $D_2$ receptor antagonists are only palliative. They tend to alleviate only certain schizophrenic behaviour, especially the "positive" symptoms of florid delusions and hallucinations, with much less effect on the "negative" symptoms of emotional withdrawal.

From receptor binding studies, it has been shown that many effective neuroleptic agents are ligands at sigma recognition sites in the brain. Various compounds are known which are capable of interacting with the sigma recognition site, and it is considered that this interaction is significant in the manifestation of their neuroleptic properties. Most of these compounds, however, also display significant activity at the dopamine $D_2$ receptor and consequently elicit the undesirable side-effects referred to above. For example, haloperidol, a widely used neuroleptic agent, interacts equally potently with sigma sites and $D_2$ receptors.

One compound which is essentially inactive at dopamine $D_2$ receptors is rimcazole. However, whilst showing some antischizophrenic activity, rimcazole displays only moderate potency at sigma sites.

The analgesic compound N-allylnormetazocine (SKF 10047), whilst having an affinity for the sigma recognition site, also interacts strongly with the N-methyl-D-aspartate (NMDA) ion-channel complex, and thereby evokes a variety of psychotic symptoms including disorientation, excitement and hallucinations.

We have now found a class of potent, selective sigma receptor antagonists displaying negligible activity at $D_2$, NMDA and other CNS receptors, which are therefore of value as neuroleptic agents.

The present invention accordingly provides the use of a compound of formula I or a pharmaceutically acceptable salt thereof:

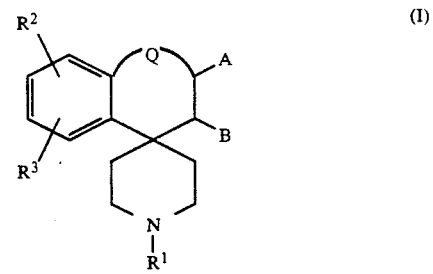

wherein

A and B each represents hydrogen, or A and B together represent a chemical bond;

Q represents a bond or a group of formula —(CH$_2$)$_2$—;

$R^1$ represents hydrocarbon;

$R^2$ and $R^3$ independently represent hydrogen, hydrocarbon, halogen, cyano, trifluoromethyl, nitro, —OR$^x$, —SR$^x$, —NR$^x$R$^y$, —CO$_2$R$^x$ or —CONR$^x$R$^y$, or together represent methylenedioxy; and $R^x$ and $R^y$ independently represent hydrogen or hydrocarbon;

for the manufacture of a medicament for the treatment and/or prevention of psychiatric disorders.

The term "hydrocarbon" as used herein includes straight-chained, branched and cyclic groups, including heterocyclic groups, containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl and heteroaryl($C_{1-6}$)alkyl.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are n-propyl, isopropyl, n-butyl and t-butyl.

Suitable alkenyl groups include straight-chained and branched alkenyl groups containing from 2 to 6 carbon atoms. Typical examples include vinyl, allyl and dimethylallyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Suitable aryl groups include phenyl and naphthyl groups.

A particular aryl($C_{1-6}$)alkyl group is benzyl.

Suitable heterocycloalkyl groups include pyrrolidinyl, piperidyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, thienyl, benzthienyl, imidazolyl, oxadiazolyl and thiadiazolyl groups. Particular heteroaryl groups are pyridyl and furyl.

The hydrocarbon group may in turn be optionally substituted by one or more groups selected from $C_{1-6}$ alkyl, adamantyl, phenyl, halogen, $C_{1-6}$ haloalkyl, trifluoromethyl, hydroxy, $C_{1-6}$ alkoxy, aryloxy, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, optionally substituted arylcarbonyloxy, $C_{2-6}$ alkylcarbonyl, optionally substituted arylcarbonyl, $C_{1-6}$ alkylthio, $C_{1-6}$ alkylsulphinyl, $C_{1-6}$ alkylsulphonyl, amino, mono- or di($C_{1-6}$)alkylamino, $C_{2-6}$ alkylcarbonylamino and $C_{2-6}$ alkoxycarbonylamino.

The term "halogen" as used herein includes fluorine, chlorine, bromine and iodine, especially chlorine.

Suitable values for the substituent $R^1$ in the compounds of formula I above include $C_{3-6}$ alkyl, $C_{2-6}$ alkenyl, aryl($C_{1-6}$)alkyl, $C_{3-7}$ cycloalkyl($C_{1-6}$)alkyl, $C_{3-7}$ heterocycloalkyl($C_{1-6}$)alkyl, and heteroaryl-($C_{1-6}$)alkyl, any of which groups may be optionally substituted. A particular group $R^1$ is benzyl.

The compound 1'-benzylspiro[indane-1,4'piperidine] is generically disclosed in JP-A-55-143980, and specifically disclosed in U.S. Pat. No. 3,125,580 as an intermediate in the preparation of a class of analgesic and mydriatic agents. There is, however, no mention of therapeutic utility for this compound in U.S. Pat. No. 3,125,580. The present invention accordingly provides a pharmaceutical composition comprising 1'-benzylspiro[indane-1,4'piperidine] or a pharmaceutically acceptable salt thereof in association with one or more pharmaceutically acceptable carriers and/or excipients.

The invention also provides 1'benzylspiro[indane-1,4'-piperidine] or a pharmaceutically acceptable salt thereof for use in therapy.

Certain compounds falling within the definition of formula I above are novel. Accordingly, in a further aspect the present invention provides a compound of formula II or a salt thereof:

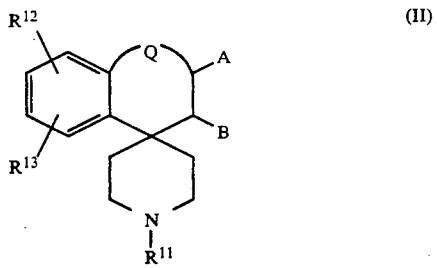

wherein
A and B each represents hydrogen, or A and B together represent a chemical bond;
Q represents a bond or a group of formula —(CH$_2$)$_2$—;
$R^{11}$ represents hydrocarbon;
$R^{12}$ and $R^{13}$ independently represent hydrogen, hydrocarbon, halogen, cyano, trifluoromethyl, nitro, —OR$^x$, —SR$^x$, —NR$^x$R$^y$, —CO$_2$R$^x$ or —CONR$^x$R$^y$, or together represent methylenedioxy; and
R$^x$ and R$^y$ independently represent hydrogen or hydrocarbon;
provided that when A and B both represent hydrogen, Q is a bond and $R^{11}$ represents alkyl, allyl, aryl, aralkyl, cycloalkyl or ar(cycloalkyl), then $R^{12}$ and $R^{13}$ do not represent hydrogen, alkoxy or hydroxyalkyl;

provided also that when Q is a bond, A, B and $R^{12}$ each represents hydrogen, and $R^{11}$ is benzyl, then $R^{13}$ does not represent methyl in the 6-position of the indane moiety;

provided also that when Q is a bond, A, B and $R^{12}$ each represents hydrogen, and $R^{11}$ is a group of formula —CH$_2$CH$_2$CXPh$_2$ in which X represents cyano or $C_{2-7}$ alkylcarbonyl, then $R^{13}$ does not represent hydrogen or methyl in the 6-position of the indane moiety.

In a still further aspect, the invention provides a pharmaceutical composition comprising a compound of formula II as defined above or a pharmaceutically acceptable salt thereof in association with one or more pharmaceutically acceptable carriers and/or excipients.

The invention also provides a compound of formula II as defined above or a pharmaceutically acceptable salt thereof for use in therapy.

For use in medicine, the salts of the compounds of formula II will be non-toxic pharmaceutically acceptable salts. Other salts may, however, be useful in the preparation of the compounds according to the invention or of their non-toxic pharmaceutically acceptable salts.

Suitable pharmaceutically acceptable salts of the compounds of formulae I and II above include acid addition salts which may, for example, be formed by mixing a solution of the compound according to the invention with a solution of a pharmaceutically acceptable non-toxic acid such as hydrochloric acid, fumaric acid, maleic acid, succinic acid, acetic acid, citric acid, tartaric acid, carbonic acid or phosphoric acid.

Subject to the above provisos, particular values for the substituent $R^{11}$ in the compounds of formula II include optionally substituted $C_{3-6}$ alkyl, for example n-butyl and n-hexyl; optionally substituted $C_{2-6}$ alkenyl, for example dimethylallyl; optionally substituted aryl($C_{1-6}$)alkyl, especially benzyl, phenethyl, methylbenzyl and methoxybenzyl; optionally substituted $C_{3-7}$ cycloalkyl($C_{1-6}$)alkyl, for example cyclohexylmethyl; optionally substituted $C_{3-7}$ heterocycloalkyl($C_{1-6}$)alkyl, for example tetrahydrofurylmethyl; and optionally substituted heteroaryl($C_{1-6}$)alkyl, for example furylmethyl and picolyl.

Subject to the above provisos, examples of the substituents $R^{12}$ and $R^{13}$ in the compounds of formula II above include hydrogen, chlorine, $C_{1-6}$ alkyl and $C_{1-6}$ alkoxy. Suitably one of $R^{12}$ and $R^{13}$ represents hydrogen and the other represents hydrogen, chlorine, methyl or methoxy, especially hydrogen or methoxy. Preferably, $R^{12}$ and $R^{13}$ both represent hydrogen. When $R^{12}$ and $R^{13}$ in the compounds of formula II above are other than hydrogen, they may be present at any desired position of the aromatic moiety.

One sub-class of compounds according to the invention is represented by the compounds of formula IIA and salts thereof:

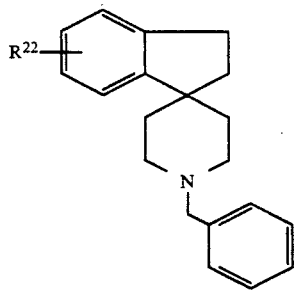

(IIA)

wherein $R^{22}$ represents $C_{1-6}$ alkyl, halogen, cyano, trifluoromethyl, nitro or hydroxy, especially methyl, chloro or hydroxy.

Another sub-class of compounds according to the invention is represented by the compounds of formula IIB and salts thereof:

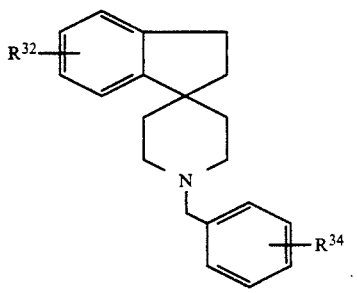

(IIB)

wherein $R^{32}$ represents hydrogen, $C_{1-6}$ alkyl, halogen, cyano, trifluoromethyl, nitro, hydroxy or $C_{1-6}$ alkoxy; and $R^{34}$ represents $C_{1-6}$ alkyl, halogen, cyano, trifluoromethyl, nitro, hydroxy or $C_{1-6}$ alkoxy. Suitably, $R^{32}$ represents hydrogen, methyl, chloro, hydroxy or methoxy; and $R^{34}$ represents methyl, chloro, nitro or methoxy. Preferably, $R^{32}$ represents hydrogen. Preferably, $R^{34}$ represents methyl or methoxy.

A further sub-class of compounds according to the invention is represented by the compounds of formula IIC and salts thereof:

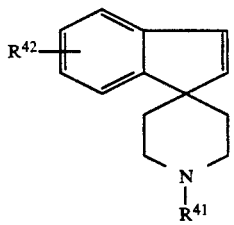

(IIC)

wherein $R^{41}$ represents $C_{3-6}$ alkyl, $C_{2-6}$ alkenyl, $C_{3-7}$ cycloalkyl($C_{1-6}$)alkyl, aryl($C_{1-6}$)alkyl, $C_{3-7}$ heterocycloalkyl($C_{1-6}$)alkyl or heteroaryl($C_{1-6}$)alkyl, any of which groups may be optionally substituted; and $R^{42}$ represents hydrogen, $C_{1-6}$ alkyl, halogen, cyano, trifluoromethyl, nitro, hydroxy or $C_{1-6}$ alkoxy. Typical values of $R^{41}$ include n-butyl, n-hexyl, dimethylallyl, benzyl, methylbenzyl, methoxybenzyl, phenethyl, cyclohexylmethyl, tetrahydrofurylmethyl and picolyl. Suitably, $R^{42}$ represents hydrogen, methyl, chloro, hydroxy or methoxy. Preferred values of $R^{41}$ include n-butyl, dimethylallyl and benzyl. Preferably, $R^{42}$ is hydrogen.

A still further sub-class of compounds according to the invention is represented by the compounds of formula IID and salts thereof:

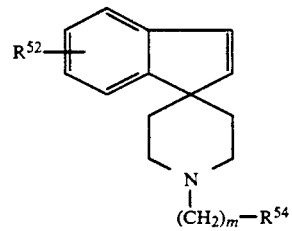

(IID)

wherein m is 1, 2 or 3, preferably 1; $R^{52}$ represents hydrogen, $C_{1-6}$ alkyl, halogen, cyano, trifluoromethyl, nitro, hydroxy or $C_{1-6}$ alkoxy; and $R^{54}$ represents $C_{3-5}$ alkenyl, $C_{3-7}$ cycloalkyl, $C_{3-7}$ heterocycloalkyl or heteroaryl, any of which groups may be optionally substituted. Suitable values of $R^{52}$ include hydrogen, methyl, chloro, hydroxy and methoxy, especially hydrogen. Particular values of $R^{54}$ include dimethylvinyl, cyclohexyl, tetrahydrofuryl and pyridyl.

A yet further sub-class of compounds according to the invention is represented by the compounds of formula IIE and salts thereof:

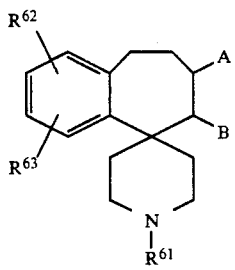

(IIE)

wherein A and B are as defined above; $R^{61}$ represents $C_{3-6}$ alkyl, $C_{2-6}$ alkenyl, $C_{3-7}$ cycloalkyl($C_{1-6}$)alkyl, aryl($C_{1-6}$)alkyl, $C_{3-7}$ heterocycloalkyl($C_{1-6}$)alkyl or heteroaryl($C_{1-6}$)alkyl, any of which groups may be optionally substituted; and $R^{62}$ and $R^{63}$ independently represent hydrogen, $C_{1-6}$ alkyl, halogen, cyano, trifluoromethyl, nitro, hydroxy or $C_{1-6}$ alkoxy, especially hydrogen, methyl, chloro, hydroxy or methoxy.

Preferably, A and B each represents hydrogen in the compounds of formula IIE above. Preferred values of $R^{61}$ are n-butyl, dimethylallyl, benzyl, methylbenzyl, phenethyl and picolyl. Preferably, $R^{62}$ and $R^{63}$ both represent hydrogen.

Specific compounds within the scope of the present invention include:

1'-(4''-methylbenzyl)spiro[indane-1,4'-piperidine];
1'-cyclohexylmethylspiro[indane-1,4'-piperidine];
1'-(4''-methoxybenzyl)spiro[indane-1,4'-piperidine];
1'-(2''-picolyl)spiro[indane-1,4'-piperidine];
1'-(2''-tetrahydrofurfuryl)spiro[indane-1,4'-piperidine];
1'-(3''-methylbut-2''-enyl)spiro[indane-1,4'-piperidine];
1'-(n-butyl)spiro[1H-indene-1,4'-piperidine];
1'-(3''-methylbut-2''-enyl)spiro[1H-indene-1,4'piperidine];
1'-benzylspiro[1H-indene-1,4'-piperidine];
1'-benzylspiro[6,7,8,9-tetrahydro-5H-benzocyclohepten-5,4'-piperidine];
1'-(n-butyl)spiro[6,7,8,9-tetrahydro-5H-benzocyclohepten-5,4'-piperidine]; and salts thereof.

In addition, the following compounds (each of which is referred to hereinafter as a "previously undisclosed compound of formula I") are not specifically disclosed in the prior art, and are therefore novel compounds according to the present invention:

1'-(n-butyl)spiro[indane-1,4'-piperidine];
1'-(n-hexyl)spiro[indane-1,4'-piperidine];
1'-(2''-phenylethyl)spiro[indane-1,4'-piperidine]; and salts thereof.

The present invention also provides a pharmaceutical composition comprising a "previously undisclosed compound of formula I" as defined above or a pharmaceutically acceptable salt thereof in association with one or more pharmaceutically acceptable carriers and/or excipients.

The present invention further provides a "previously undisclosed compound of formula I" as defined above or a pharmaceutically acceptable salt thereof for use in therapy.

The pharmaceutical compositions of this invention are preferably in unit dosage forms such as tablets, pills, capsules, powders, granules, sterile parenteral solutions or suspensions, or suppositories, for oral, parenteral or rectal administration. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinylpyrrolidone or gelatin.

In the treatment of psychiatric disorders, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds of formula I above wherein A and B each represents hydrogen, including the novel compounds according to the invention, may be prepared by a process which comprises reducing a compound of formula III:

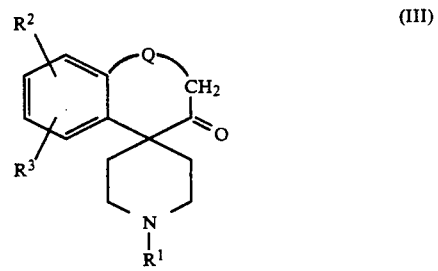

(III)

wherein Q, $R^1$, $R^2$ and $R^3$ are as defined above.

The ketone of formula III may conveniently be reduced directly to the corresponding compound of formula I wherein A and B each represents hydrogen by the Wolff-Kishner method. This comprises treating the hydrazone derivative of the ketone of formula III with a strong base, e.g. potassium hydroxide, in a suitable solvent, such as diethylene glycol, at an elevated temperature, preferably the reflux temperature of the solvent. Q is —(CH$_2$)$_2$— may conveniently be prepared by a method analogous to that described in *J. Org. Chem.*, 1966, 31, 3345. This comprises reacting a compound of formula $R^1$—N[(CH$_2$)$_2$)$_2$Z]$_2$ with a compound of formula IV:

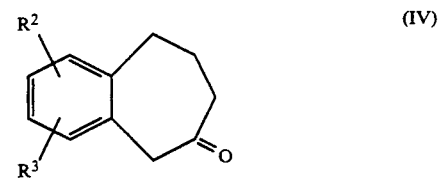

(IV)

wherein $R^1$, $R^2$ and $R^3$ are as defined above; and Z represents a leaving group, e.g. chlorine.

The reaction is carried out in the presence of a strong base such as potassium t-butoxide, in a suitable solvent, for example dimethyl sulphoxide/t-butanol, suitably at room temperature.

The compounds of formula IV above, where they are not commercially available, can be prepared by the methods described in, for example, *Russ. Chem. Rev.* (Engl. Transl.), 1966, 35, 523; *J. Org. Chem.*, 1968, 33, 4288; *Tetrahedron Lett.*, 1971, 951; or *J. Med. Chem.*, 1989, 32, 961; or by methods analogous thereto.

The compounds of formula I above wherein A and B together represent a chemical bond, including the novel compounds according to the invention, may be prepared by a process which comprises dehydrating a compound of formula V:

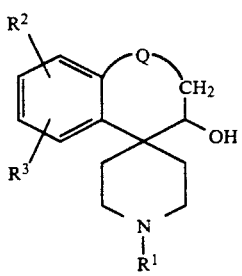

wherein Q, $R^1$, $R^2$ and $R^3$ are as defined above.

A suitable dehydrating reagent for effecting the above conversion will, for example, be phosphorus oxychloride in the presence of pyridine.

The hydroxy intermediates of formula V above may conveniently be prepared by reduction of the keto group in the corresponding intermediate of formula III above using, for example, sodium borohydride under standard conditions.

An alternative process for preparing the compounds of formula I above, including the novel compounds according to the invention, comprises reacting a compound of formula $R^1$-L with a compound of formula VI:

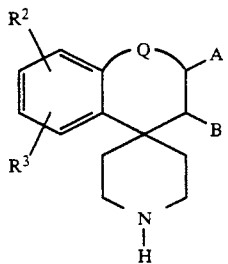

wherein A, B, Q, $R^1$, $R^2$ and $R^3$ are as defined above; and L represents a leaving group.

The leaving group L is suitably halogen, for example bromine.

The reaction is conveniently carried out in the presence of a mild base such as potassium carbonate, in a suitable solvent, e.g. N,N-dimethylformamide, suitably at an elevated temperature, for example a temperature in the region of 100° C.

The compounds of formula VI above wherein A and B each represents hydrogen may be prepared by a process which comprises reducing a compound of formula VII:

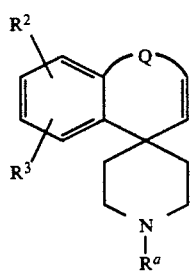

wherein Q, $R^2$ and $R^3$ are as defined above, and $R^a$ represents hydrogen or an amino-protecting group; and subsequently, if necessary, removing the amino-protecting group $R^a$.

An appropriate method for reducing the intermediate of formula VII is catalytic hydrogenation. A suitable catalyst is palladium hydroxide on charcoal, and the reaction is conveniently carried out in formic acid/ethanol as solvent.

Suitable examples of amino-protecting groups for the substituent Ra include carboxylic acid groups such as acetyl, chloroacetyl, trifluoroacetyl, formyl, benzoyl, phthaloyl, phenylacetyl or pyridinecarbonyl; acid groups derived from carbonic acid such as ethoxycarbonyl, benzyloxycarbonyl, t-butoxycarbonyl, biphenylisopropoxycarbonyl, p-methylbenzyloxycarbonyl, p-nitrobenzyloxycarbonyl, p-bromobenzyloxycarbonyl, p-phenylazobenzyloxycarbonyl, p-(p'-methoxyphenylazo)benzyloxycarbonyl or t-amyloxycarbonyl; acid groups derived from sulphonic acid, e.g. p-toluenesulphonic acid; and other groups such as benzyl, trityl, o-nitrophenylsulphenyl or benzylidene.

Preferred amino-protecting groups are benzyl, benzyloxycarbonyl and t-butoxycarbonyl.

The removal of the amino-protecting group present in the resultant compound may be effected by an appropriate procedure depending upon the nature of the protecting group. For example, if $R^a$ represents t-butoxycarbonyl this group may be removed by treatment with a mineral acid, e.g. gaseous HCl. Alternatively, if $R^a$ represents benzyl this group may be removed in situ during hydrogenation of the intermediate of formula VII.

The intermediates of formula VII above wherein Q represents a bond may be prepared by a process which comprises reacting a compound of formula $Ra—N[(CH_2)_2Z]_2$ with an indene derivative of formula VIII:

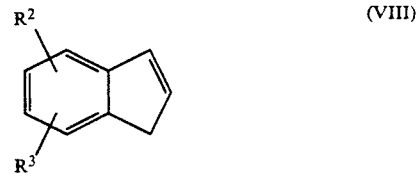

wherein $R^2$, $R^3$, $R^a$ and Z are as defined above; and subsequently, if desired, removing the amino-protecting group $R^a$.

The reaction is carried out in the presence of a strong base such as lithium bis(trimethylsilyl)amide, in a suitable solvent, e.g. tetrahydrofuran, suitably at a temperature in the region of 0° C.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene, *Protective Groups in Organic Synthesis*. John Wiley & Sons, 1981. The protecting groups may be removed at a convenient subsequent stage using methods known from the art.

Displacement of Tritiated Sigma Ligand

In vitro activity

Binding of test compounds to the sigma site in vitro was determined by the method of Weber et al., *Proc.*

Natl. Acad. Sci. U.S.A., 1986, 83, 8784. The compounds of each of the accompanying Examples displaced tritiated di-tolyl guanidine (DTG) from sigma sites with potencies better than 200 nM.

EXAMPLE 1

1'-Benzylspiro[indane-1,4''-piperidine]

Triethylamine (74 ml, 0.58 mol) was added dropwise, over 1 hour, to a stirred solution of di-tert-butyldicarbonate (125 g, 0.57 mol) and bis(2-chloroethyl)amine hydrochloride (85 g, 0.48 mol) in dichloromethane (600 ml). After 1 hour more triethylamine (6 ml, 0.04 mol) was added, and the mixture stirred overnight, under nitrogen. The solvent was evaporated and the resulting oil taken up in ether (500 ml) and washed with water (500 ml). The organic phase was separated and the aqueous layer extracted with ether (500 ml). The ethereal layers were combined, dried (MgSO$_4$) and evaporated in vacuo. The crude residue was chromatographed in 1:1 petrol:ether, to give N-tert-butyloxycarbonylbis (2-chloroethyl)amine (102 g, 88%) as a pale yellow oil. N.M.R. (CDCl$_3$) δ 1.48 (9H, s), 3.65 (4H, m). m/z (CI, NH$_3$), 242/244 (M+1), 205, 203, 188, 186, 168, 106, 92.

Step 2: 1'-(tert-Butyloxycarbonyl)spiro [indene-1,4'-piperidine]

To a solution of indene (5.1 ml, 0.04 mol) in dry tetrahydrofuran (15 ml), cooled in an ice bath and maintained under an atmosphere of nitrogen, was added lithium bis (trimethylsilyl) amide (82 ml of a 1.0M solution in tetrahydrofuran, 0.08 mol), over 15 minutes. The mixture was stirred in the cold for 30 minutes, then added dropwise to a solution of N-tert-butyloxycarbonylbis (2-chloroethyl)amine (9.9 g, 0.04 mol) in tetrahydrofuran (200 ml), at 0° C. The mixture was stirred for 2 hours at this temperature, then allowed to warm to ambient temperature and stirred for a further 30 minutes. The solvent was removed in vacuo to leave a dark oil, which was chromatographed using 5:1 petrol:ether as the eluant, to give 1'-(tert-butyloxycarbonyl)spiro[indene-1,4'-piperidine] (7.1 g, 58%) as a pale yellow solid. N.M.R. (CDCl$_3$)δ 1.28 (2H, d, J=12 Hz), 1.50 (9H, s), 2.00 (2H, t of d, J=12 and 4 Hz), 3.13 (2H, t of d, J=12 and 2 Hz), 4.20 (2H, m), 6.79 (1H, d, J=6 Hz), 6.84 (1H, d, J=6 Hz), 7.30 (4H, m).

Step 3: Spiro[indane-1,4'-piperidine]hydrochloride

A solution of 1'-(tert-butyloxycarbonyl)spiro[indene-1,4'-piperidine] (3.0 g, 0.011 mol) in ethyl acetate (150 ml) was stirred at 0° C., and treated with hydrogen chloride for 30 minutes. The mixture was then evaporated to dryness, ethyl acetate (100 ml) was added, then removed in vacuo three times. The residue was stirred with anhydrous ether (200 ml), and the solid filtered off, to give spiro[indene-1,4'-piperidine] hydrochloride (2.3 g, 99%) as a pale yellow solid. The product was not purified further.

A solution of spiro[indene-1,4'-piperidine]hydrochloride (1.9 g, 8.6 mmol) in ethanol (50 ml) was hydrogenated at 50 p.s.i. for 1 hour, in the present of 10% palladium on carbon (0.3 g, 16% (w/w)). The catalyst was filtered off, and the ethanol removed in vacuo. The remaining solid was recrystallised from 4:1 ethyl acetate:ethanol to give spiro[indane-1,4'-piperidine] hydrochloride (814 mg, 43%) as a white crystalline solid. N.M.R. (D$_2$O)δ 1.79 (2H, d, J=14 Hz), 2.06 (2H, t of d, J=14 and 4 Hz), 2.14 (2H, t, J=7 Hz), 2.98 (2H, t, j=7 Hz), 3.25 (2H, t of d, J=14 and 2 Hz), 3.48 (2H, m), 7.33 (4H, m)

Step 4: Spiro[indane-1,4'-piperidine]

Spiro[indane-1,4'-piperidine]hydrochloride (0.4 g, 1.8 mmol) was dissolved in water (20 ml), and the solution made alkaline using solid sodium carbonate. The mixture was extracted with ethyl acetate (5×20 ml), and the organic layers combined and dried (MgSO$_4$). The solvent was removed in vacuo to give spiro[indane-1,4'-piperidine] as a clear oil, which was used without further purification.

Step 5: 1'-Benzylspiro[indane-1,4'-piperidine]

To a stirred solution of spiro[indane-1,4'-piperidine] (110 mg, 0.59 mmol), in anhydrous DMF (10 ml), under an atmosphere of nitrogen, was added potassium carbonate (98 mg, 0.71 mmol) followed by benzyl bromide (0.08 ml, 0.65 mmol) dropwise. The mixture was heated at 100° C. for 2 hours, after which time the solution was cooled to ambient temperature. The solvent was removed in vacuo, then ether (20 ml) was added to the residue and the mixture was washed with water (2×20 ml). The organic layer was separated, dried (MgSO$_4$) and the solvent evaporated in vacuo. The crude residue was chromatographed using 1:1 petrol (60/80):ether, to give 1-benzylspiro[indane-1,4'-piperidine] as a viscous colourless oil (31 mg, 20%).

The hydrochloride salt was prepared using ethereal hydrogen chloride, which, after evaporation of the solvent in vacuo, gave the title compound hydrochloride (24 mg, 70%) as a white solid, after recrystallisation from 4:1 ethyl acetate:ethanol. m.p. 270°-274° C. (sublimed). NMR (D$_2$O)δ 1.80 (2H, br d, J=14 Hz), 2.06 (4H, m), 2.96 (2H, t, J=7 Hz), 3.24 (2H, br t, J=13 Hz), 3.55 (2H, br d, J=11.5 Hz), 4.37 (2H, s), 7.30 (4H, m), 7.53 (5H, br s). m/z (EI) 277 (M+), 200, 146, 91.

EXAMPLE 2

1'-n-Butylxpiro[indane-1,4'-piperidine]

In the same way as that described in Example 1, step 5, the title compound was prepared using spiro[indane-1,4'-piperidine] (77 mg, 0.41 mmol), DMF (10 ml), potassium carbonate (68 mg, 0.49 mmol), and n-butyl iodide (0.05 ml, 0.45 mmol). The crude residue was chromatographed using 5:95 methanol: dichloromethane, to give 1'-n-butylspiro[indane-1,4'-piperidine] (53 mg, 53%) as a beige solid.

The hydrochloride salt was prepared using ethereal hydrogen chloride, to give the title compound hydrochloride (28 mg, 46%) as white needles, after recrystallisation from 4:1 ethyl acetate: ethanol. m.p. 230°-234° C. NMR (D$_2$O) δ 0.96 (3H, t, J=7 Hz), 1.41 (2H, m, J=7 Hz), 1.76 (4H, m), 2.14 (4H, m), 2.98 (2H, t, J=7 Hz), 3.18 (4H, m), 3.62 (2H, m), 7.32 (4H, m). m/z (EI), 243 (M+), 200, 128.

EXAMPLE 3

1'-(4''-Methylbenzyl)spiro[indane-1,4'-piperidine]

In the same way as that described in Example 1, step 5, 1'-(methylbenzyl)spiro[indane-1,4'-piperidine] was prepared using spiro[indane-1,4'-piperidine] (0.25 g, 1.3 mmol), DMF (10 ml), potassium carbonate (0.24 g, 1.7 mmol) and 4-methylbenzyl bromide (1.7 mmol, 0.32 g). The crude residue was chromatographed using 1:1 petrol:ether to give the title compound (0.1 g, 26%) as a white crystalline solid.

The hydrochloride salt of the title amine (94 mg, 0.32 mmol) was prepared using ethereal hydrogen chloride, to give 1'-(methylbenzyl)spiro[indane-1,4'-piperidine] (56 mg, 53%) as white crystals, after recrystallisation from ethanol/ethyl acetate. m.p. 284°–286° C. N.M.R. (D$_2$O) δ 180 (2H, br d, J=14 Hz), 2.10 (4H, m), 2.38 (3H, s), 295 (2H, t, J=7 Hz), 3.21 (2H, br t, J=13 Hz), 3.52 (2H, m), 4.32 (2H, s), 7.26–7.43 (8H, m). m/z (CI, NH$_3$), 292 (M+), 186, 160, 105.

EXAMPLE 4

1'-Cyclohexylmethylspiro[indane-1,4'-piperidine]

In the same way as that described in Example 1, step 5, 1'-cyclohexylmethylspiro[indane-1,4'-piperidine] was prepared using spiro[indane-1,4'-piperidine] (0.4 g, 2.2 mmol), DMF (20 ml), potassium carbonate (326 mg, 2.4 mmol) and cyclohexylmethyl bromide (0.51 g, 2.9 mmol). The crude residue was chromatographed using 1:1 petrol:ether, to give the title compound (433 mg, 69%) as a beige solid.

The hydrochloride salt was prepared using ethereal hydrogen chloride, to give the title compound hydrochloride (334 mg, 68%) as a white solid. m.p. 304°–306° C. N.M.R. (D$_2$O) δ 1.00–1.36 (5H, m), 1.67–1.91 (8H, m), 2.16 (4H, m), 3.00 (4H, m), 3.17 (2H, t, J=11 Hz), 3.60 (2H, d, J=13 Hz), 7.30 (4H, m). m/z (CI, NH$_3$), 284 (M+1), 200.

EXAMPLE 5

1'-(4"-Methoxybenzyl)spiro[indane-1,4'-piperidine]

In the same way as that described in Example 1, and step 5, 1'-(4"-methoxybenzyl)spiro[indane-1,4'-piperidine] was prepared using spiro[indane-1,4'-piperidine] (0.4 g, 2.2 mmol), DMF (20 ml), potassium carbonate (326 mg, 2.4 mmol) and 4-methoxybenzyl chloride (0.4 ml, 3.1 mmol). the crude residue was chromatographed using 1:1 petrol:ether, to give the title amine (459 mg, 67%) as a white solid.

The hydrochloride salt was prepared, using ethereal hydrogen chloride, to give 1'-(4"-methoxybenzyl)spiro[indane-1,4'-piperidine] hydrochloride (207 mg, 52%) as a white solid. m.p. 259°–261° C. N.M.R. (D$_2$O-D$_6$-DMSO). δ 1.79 (2H, d, J=14 Hz), 2.10 4H, m), 2.96 (2H, t, J=7 Hz), 3.21 (2H, m), 3.49 (2H, m), 3.88 (3H, s), 4.08 (2H, s), 7.11 (2H, d, J=9 Hz), 7.30 (4H, m), 7.49 (2H, d, J=9 Hz). m/z (EI), 307 (M+), 186, 121, 91, 77.

EXAMPLE 6

1'Hexylspiro[indane-1,4'-piperidine]

In the same way as that described in Example 1, step 5, the title compound was synthesised using spiro[indane-1,4'-piperidine] (0.4 g, 2.2 mmol), DMF (15 ml), potassium carbonate (0.33 g, 2.4 mmol) and iodohexane (0.62 g, 2.9 mmol). The crude residue was chromatographed in 1:1 petrol:ether to give 1'-hexylspiro[indane-1,4'-piperidine] (314 mg, 52%) as a pale yellow oil.

The hydrochloride salt of the title amine (300 mg, 1.1 mmol) was prepared using ethereal hydrogen chloride, to give 1'-hexylspiro[indane-1,4'-piperidine]hydrochloride (177 mg, 52%) as white crystals, after recrystallisation from ethyl acetate/ethanol. m.p. 283°–287° C. N.M.R. (D$_2$O) δ 0.89 (3H, t, J=7 Hz), 1.35 (6H, m), 1.79 (4H, m), 2.13 (4H, m), 298 (2H, t, J=7 Hz), 3.17 (4H, m), 3.60 (2H, m) 7.31 (4H, m). m/z (CI, NH$_3$), 272 (M+1), 200.

EXAMPLE 7

1'-(2"-Picolyl)spiro[indane-1,4'-piperidine]

In the same way as that described in Example 1, step 5, 1'-(2"-pilolyl)spiro[indane-1,4'-piperidine] was prepared using spiro[indane-1,4'-piperidine] (0.4 g, 2.2 mmol), DMF (15 ml), potassium carbonate (0.65 g, 4.7 mmol) and picolyl chloride hydrochloride (0.4 g, 2.4 mmol). The crude residue was chromatographed using 95:5 dichloromethane: methanol to afford the title compound (350 mg, 56%) as a red oil.

The hydrochloride salt was prepared by treating the title amine (340 mg, 1.2 mmol) with ethereal hydrogen chloride. 1'-(2"-Picolyl)spiro[indane-1,4'-piperidine] hydrochloride (299 mg, 78%) was isolated as white crystals, after recrystallisation from ethyl acetate/ethanol. m.p. 208°–212° C. N.M.R. (D$_2$O) δ 1.83 (2H, d, J=13 Hz), 2.13 (4H, m), 2.97 (2H, t, J=7 Hz), 3.39 (2H, t, J=12 Hz), 3.59 (2H, m), 4.62 (2H, s), 7.34 (4H, m), 7.75 (1H, dd, J=8 and 5 Hz), 7.85 (1H, d, J=8 Hz), 8.24 (1H, t, J=8 Hz), 8.79 (1H, d, J=5 Hz). m/z (CI, NH$_3$), 279 (M+1), 186, 131, 115, 93.

EXAMPLE 8

1'-(2"-Tetrahydrofurfuryl)sprio[indane-1,4'-piperidine]

In the same way as that described in Example 1, step 5, 1'-(2"-tetrahydrofurfuryl)spiro[indane-1,4'-piperidine] was prepared, using spiro[indane-1,4'-piperidine] (0.4 g, 2.2 mmol), DMF (15 ml), potassium carbonate (0.33 g, 2.4 mmol) and tetrahydrofurfuryl bromide (0.4 ml, 2.9 mmol). The crude residue was chromatographed using 1:1 petrol:ether eluant to give 1'-(2"-tetrahydrofurfuryl)spiro[indane-1,4'-piperidine] (170 mg, 28%) as a colourless oil.

The hydrochloride salt was prepared by treating the title amine (165 mg, 0.61 mol) with ethereal hydrogen chloride, to give the title compound hydrochloride (89 mg, 48%) as a white crystalline solid, after recrystallisation from ethyl acetate/ethanol. m.p. 215°–219° C., N.M.R. (D$_2$O) δ 1.70 (1H, m), 1.87 (2H, m), 1.98 (2H, m), 2.20 (5H, m), 2.99 (2H, t, J=7 Hz), 3.23 (4H, m), 3.64 (2H, m), 3.94 (2H, m), 4.95 (1H, m), 7.32 (4H, m). m/z (EI), 271 (M+), 200.

EXAMPLE 9

1'-(2"-Phenylethyl)spiro[indane-1,4'-piperidine]

In the same way as that described in Example 1, step 5, 1'-(2"-phenylethyl)spiro[indane-1,4'-piperidine] was prepared, using spiro[indane-1,4'-piperidine] (0.4 g, 2.2 mmol), DMF (15 ml), potassium-carbonate (0.33 g, 2.4 mmol) and phenethyl bromide (0.4 ml, 2.9 mmol). The crude residue was chromatographed using 1:1 petrol:ether to give the title amine (440 mg, 68%) as a pale yellow oil.

The hydrochloride salt was prepared by treating the title compound (430 mg, 1.5 mmol) with ethereal hydrogen chloride, to give 1'-(2"-phenylethyl)spiro[[indane-1,4'-piperidine] (343 mg, 71%) as a white crystalline solid after recrystallisation from ethyl acetate/ethanol. m.p. 287°–290° C. N.M.R. (D$_6$-DMSO) δ 1.67 (2H, d, J=14 Hz), 2.07 (2H, t, J=7 Hz), 2.26 (2H, m), 2.90 (2H, t, J=7 Hz), 3.12 (4H, m), 3.31 (2H, m), 3.57 (2H, d, J=11 Hz), 7.24 (9H, m), 10.82 (1H, br s). m/z (CI, NH$_3$), 292 (M+1), 200.

EXAMPLE 10

1'-(3"-Methylbut-2"-enyl)spiro[indane-1,4'-piperidine]

To a stirred solution of spiro[indane-1,4'-piperidine] (0.23 g, 1.25 mmol) in dichloromethane (20 ml), under an atmosphere of nitrogen, was added 4-bromo-2-methylbut-2-ene (0.24 g, 1.6 mmol). The solution was stirred at room temperature for 3 hours, then saturated sodium bicarbonate solution (20 ml) was added. The organic layer was separated, dried (MgSO$_4$) and evaporated in vacuo. The crude residue was chromatographed in 10:90 methanol:dichlorometane to give 1'-(3"-methylbut-2"-enyl)spiro[indane-1,4'-piperidine] (156 mg, 50%) as a white crystalline solid.

The hydrochloride salt of the title amine (130 mg, 0.51 mmol) was prepared using ethereal hydrogen chloride, to give 1'-(3"-methylbut-2"-enyl)spiro[indane-1,4'-piperidine] (85 mg, 57%) as white crystals, after recrystallisation from ethyl acetate/ethanol. m.p. 264°-266° C. N.M.R. (D$_2$O) δ 1.78-1.86 (8H, m), 2.12 (4H, m), 2.98 (2H, t, J=7 Hz), 3.16 (2H, br t, J=13 Hz), 3.58 (2H, m), 3.77 (2H, d, J=8 Hz), 5.35 (1H, br t, J=8 Hz), 7.35 (4H, m). m/z (CI, NH$_3$), 256 (M+1), 201, 129, 110.

EXAMPLE 11

1'-Butylspiro[1H-indene-1,4'-piperidine]

Step 1: Spiro[1H-indene-1,4'-piperidine]

Spiro[1H-indene-1,4'-piperidine]hydrochloride (400 mg, 1.8 mmol), prepared according to Example 1, step 3, was dissolved in water (10 ml), and the solution made alkaline with sodium carbonate. The mixture was extracted with dichloromethane (3×10 ml), the organic layers separated, dried (MgSO$_4$) and evaporated in vacuo. The free base was used without any further purification.

Step 2: 1'-Butylspiro[1H-indene1,4'-piperidine]

In the same way as that described in Example 1, step 5, the title compound was prepared, using spiro[1H-indene-1,4'-piperidine] (333 mg, 1.8 mmol), DMF (15 ml), potassium carbonate (0.26 g, 1.9 mmol) and iodobutane (267 μl, 2.4 mmol). The crude residue was chromatographed in dichloromethane:methanol 95:5, to give 1'-butylspiro[1H-indene-1,4'-piperidine] (136 mg, 31%) as a clear oil.

The hydrochloride salt was prepared using ethereal hydrogen chloride, to give the title amine hydrochloride (91 mg, 58%) as a white crystalline solid, after recrystallisation from ethyl acetate/ethanol. m.p. 276°-280° C. N.M.R. (D$_2$O) δ 0.98 (3H, t, J=6 Hz), 1.45 (2H, m), 1.52 (2H, m), 1.80 (2H, m), 2.45 (2H, t of d, J=14 and 2 Hz), 3.28 (4H, m), 3.74 (2H, m), 6.98 (1H, d, J=6 Hz), 7.04 (1H, d, J=6 Hz), 7.38 (2H, m), 7.48 (2H, m). m/z (EI), 241 (M+), 198, 155, 141, 128, 112, 99, 81, 69.

EXAMPLE 12

1'-(3"-Methylbut-2"-enyl)spiro[1H-indene-1,4'-piperidine]

To a stirred solution of spiro[1H-indene-1,4'-piperidine] (422 mg, 2.2 mmol) in dichloromethane, at 0° C. under nitrogen, was added 4-bromo-2-methylbut-2-ene (233 μl, 2.0 mmol) dropwise over 15 minutes. The mixture was stirred at 0° C. for 45 minutes before adding saturated sodium bicarbonate solution until alkaline. The organic phase was separated, dried (MgSO$_4$), and evaporated in vacuo. The crude residue was chromatographed in 95:5 dichloromethane:methanol to give 1'-(3"-methylbut-2"-enyl)spiro[1H-indene-1,4'-piperidine] (259 mg, 45%) as a beige solid.

The hydrochloride salt was prepared using ethereal hydrogen chloride, to give the title compound hydrochloride (113 mg, 38%) as white crystals, after recrystallisation from ethyl acetate/ethanol. m.p. 265°-267° C. N.M.R. (D$_2$O) δ 1.53 (2H, d, J=14 Hz), 1.81 (3H, s), 1.87 (3H, s), 2.41 (2H, t of d, J=14 and 4 Hz), 3.29 (2H, t of d, J=13 and 3Hz), 3.71 (2H, m), 3.84 (2H, d, J=8 Hz), 5.38 (1H, t, J=8 Hz), 6.97 (1H, d, J=6 Hz), 7.02 (1H, d, J=6 Hz), 7.36 (2H, m), 7.48 (2H, M). m/z (EI), 253 (M+), 238, 185, 155, 141, 128, 112, 91, 69.

EXAMPLE 13

1'-Benzylspiro[1H-indene-1,4'-piperidine]

To a stirred solution of potassium tert-butoxide (1.93 g, 17 mmol) in dimethyl sulphoxide (30 ml), under an atmosphere of nitrogen, was added a solution of N-benzylbis (2-chloroethylamine) (2.2 g, 9.5 mmol) and indene (1.0 g, 8.6 mmol) in tert-butanol (2ml), over a period of 15 minutes. The solution was stirred for 24 hours at ambient temperature then 10% hydrochloric acid was added cautiously until pH1. The mixture was diluted with ether (50 ml), and washed with water (50 ml). The aqueous layer was separated, and the organic layer washed once more with 10% hydrochloric acid (50 ml). The aqueous layers were combined, made alkaline with sodium carbonate, then extracted with ethyl acetate (5×50 ml). The combined organic layers were dried (MgSO$_4$) and evaporated in vacuo. The crude residue was chromatographed in 1:1 petrol:ether to give 1'-benzylspiro[1H-indene-1,4'-piperidine] (632 mg, 27%) as a yellow oil.

The hydrochloride salt was prepared using ethereal hydrogen chloride to give the title amine hydrochloride (256 mg, 36%) as white crystals, after recrystallisation from ethyl acetate/ethanol. m.p. 270°-274° C. N.M.R. (D$_2$O) δ 1.52 (2H, d, J=15 Hz), 2.39 (2H, t of d, J=14 and 3Hz), 3.37 (2H, t, J=11 Hz), 3.67 (2H, m), 4.45 (2H, s), 6.97 (1H, d, J=6 Hz), 7.01 (1H, d, J=6 Hz), 7.32 (2H, m), 7.45 (2H, m), 7.57 (5H, s). m/z (EI), 275 (M+), 256, 234, 208, 180, 125, 110, 91, 81, 69.

EXAMPLE 14

1'-Benzylspiro[6,7,8,9-tetrahydro-5H-benzocyclohepten-5,4'-piperidine]

Step 1:
1'-Benzylspiro[5,7,8,9-tetrahydro-6H-Benzocyclohepten-6-on-5,4'-piperidine]

A stirred solution of bis (2-chloroethyl) amine hydrochloride (150 g, 0.84 mol), potassium carbonate (255 g, 1.9 mol) and benzyl bromide (110 ml, 0.92 mol) in DMF (1500 ml) was heated at 100° C. for 1 hour. The mixture was allowed to cool to ambient temperature, then the DMF removed in vacuo. The residue was taken into ethyl acetate (1000 ml), then washed with water (2×1000 ml). The organic phase was separated, dried (MgSO$_4$) and evaporated. The crude residue was chromatographed in 20:1 petrol:ether, to give N-benzyl bis(2-chloroethyl)amine (36 g, 18%) as a pale yellow oil.

To a stirred solution of potassium tert-butoxide (5.9 g, 52.4 mmol) in dimethyl sulphoxide (74 ml), under an atmosphere of nitrogen, was added a solution of 5,7,8,9-tetrahydro-6H-benzocyclohepten-6-one (4.2 g, 26 mmol) and N-benzyl bis (2-chloroethyl)amine (6.1 g, 26 mmol) in tert-butanol (9 ml), over a period of 1 hour. The solution was stirred for 18 hours at ambient temperature then 6% hydrochloric acid was added cautiously, until pH1. The mixture was diluted with ether (200 ml) and washed successively with water (200 ml) and 6% hydrochloric acid (50 ml). The aqueous layers were combined, made alkaline with solid sodium carbonate, then extracted with ethyl acetate (3×100 ml). The combined organic layers were dried (MgSO$_4$) and evaporated in vacuo. The crude residue was chromatographed in 1:1 petrol:ether to give 1'-benzyl-spiro[5,7,8,9-tetrahydro-6H-benzocyclohepten-6-on-5,4'-piperidine] (0.56 g, 7%) as a pale yellow oil. NMR (CDCl$_3$) δ 1.98 (2H, m), 2.12 (2H, m), 2.26 (2H, m), 2.42 (2H, t of d, J=13 and 3Hz), 2.56 (2H, t, J=7 Hz), 2.73 (2H, m), 2.85 (2H, t, J=7 Hz), 3.52 (2H, s), 7.05–7.39 (8H, m), 7.50 (1H, d, J=9 Hz). m/z (EI), 3.19 (M+), 2.51, 186, 146, 108, 91.

Step 2:
1'Benzylspiro[6,7,8,9-tetrahydro-5H-benzocyclohepten-5,4'-piperidine]

A solution of 1'-benzylspiro[5,7,8,9-tetrahydro-6H-benzocyclohepten-6-on-5,4'-piperidine](0.56 g, 1.88 mmol), hydrazine hydrate (0.31 ml, 6.3 mmol) and potassium hydroxide (0.35 g, 6.3 mmol) in diethylene glycol (10 ml) was heated at reflux for 2 hours. After this time the reflux condenser was replaced by an air condenser, and heating continued for a further 2 hours. The solution was finally heated at reflux for 3 hours and then allowed to cool to ambient temperature. The mixture was diluted with ethyl acetate (100 ml) and washed with water (50 ml). The organic layer was separated, and the aqueous phase washed with ethyl acetate (2×50 ml). The organic layers were combined, washed with brine (100 ml), dried (MgSO$_4$) and evaporated under reduced pressure. The brown residue was chromatographed in 1:1 petrol:ether to give 1'-benzylspiro[6,7,8,9-tetrahydro-5H-benzocyclohepten-5,4'-piperidine] (305 mg, 57%) as a pale yellow oil. NMR (CDCl$_3$) δ 1.77 (6H, m), 1.96 (2H, m), 2.09 (2H, m), 2.40 (2H, t of d, J=14 and 4 Hz), 2.64 (2H, m), 2.94 (2H, m), 3.51 (2H, s), 7.05–7.37 (9H, m). m/z (CI, NH$_3$), 306 (M+1), 174, 91.

EXAMPLE 15

1'-Butylspiro[6,7,8,9-tetrahydro-5H-benzocyclohepten-5,4'-piperidine]

Step 1:
Spiro[6,7,8,9-tetrahydro-5H-benzocyclohepten-5,4'-piperidine]

A solution of 1'-benzylspiro[6,7,8,9-tetrahydro-5H-benzocyclohepten-5,4'-piperidine] (526 mg, 1.7 mmol) in ethanol (100 ml), containing formic acid (6 ml), was hydrogenated at 50 p.s.i. in the presence of palladium hydroxide on carbon (Pearlman's catalyst) (250 mg, 505 (w/w)) for 6 hours. The solution was filtered and the solvents removed in vacuo. The residue was taken up in ethyl acetate (50 ml) and washed with 10% (w/v) potassium hydroxide in water (50 ml). The organic phase was separated and the aqueous layer extracted once more with ethyl acetate (50 ml). The combined organic layers were dried (MgSO$_4$) and the solvents removed in vacuo to give spiro [6,7,8,9-tetrahydro-5H-benzocyclohepten-5,4'-benzocyclohepten-5,4'-piperidine] (240 mg, 65%), which was sued without further purification.

Step 2:
1'-Butylspiro[6,7,8,9-tetrahydro-5H-benzocyclohepten-5,4'-piperidine]

In the same way as that described in Example 1, step 5, 1'-butylspiro[6,7,8,9-tetrahydro-5H-benzocyclohepten-5,4'-piperidine] was prepared, using spiro[6,7,8,9-tetrahydro-5H-benzocyclohepten-5,4'-piperidine] (230 mg, 1.1 mmol), DMF (20 ml), potassium carbonate (163 mg, 1.2 mmol) and iodobutane (0.16 ml), 1.4 mmol). The crude residue was chromatographed (eluant 95:5 dichloromethane:methanol) to give the title amine (80 mg, 28%) as a pale yellow solid.

The hydrochloride salt was prepared using ethereal hydrogen chloride to give 1'-butylspiro[6,7,8,9-tetrahydro-5H-benzocyclohepten-5,4'-piperidine]hydrochloride (52 mg, 58%) as white crystals, after recrystallisation from ethyl acetate/ethanol. m.p. 288°–294° C. N.M.R. (D$_2$O) δ 0.94 (3H, m), 1.34 (2H, m) 1.72 (9H, m), 2.08 (1H, br t, J=12 Hz), 2.44 (1H, brd, J=14 Hz), 2.83 (1H, m), 3.01 (3H, m), 3.20 (3H, m), 3.56 (2H, m), 7.32 (4H, m). m/z (EI), 271 (M+), 228, 208, 180, 152, 129.

EXAMPLE 16

Tablet Preparation

Tablets containing 1.0, 2.0, 25.0, 26.0, 50.0 and 100.0 mg, respectively of the following compounds are prepared as illustrated below:
1'-(4''-Methylbenzyl)spiro[indane-1,4'-piperidine]
1'-(3''-Methylbut-2''-enyl)spiro[indane-1,4'-piperidine]
1'-Benzylspiro[6,7,8,9-tetrahydro-5H-benzocyclohepten-5,4'-piperidine]

| TABLE FOR DOSES CONTAINING FROM 1–25 MG OF THE ACTIVE COMPOUND | | | |
|---|---|---|---|
| | Amount-mg | | |
| Active Compound | 1.0 | 2.0 | 25.0 |
| Microcrystalline cellulose | 49.25 | 48.75 | 37.25 |
| Modified food corn starch | 49.25 | 48.75 | 37.25 |
| Magnesium stearate | 0.50 | 0.50 | 0.50 |

| TABLE FOR DOSES CONTAINING FROM 26–100 MG OF THE ACTIVE COMPOUND | | | |
|---|---|---|---|
| | Amount-mg | | |
| Active Compound | 26.0 | 50.0 | 100.0 |
| Microcrystalline cellulose | 52.0 | 100.0 | 200.0 |
| Modified food corn starch | 2.21 | 4.25 | 8.5 |
| Magnesium stearate | 0.39 | 0.75 | 1.5 |

All of the active compound, cellulose, and a portion of the corn starch are mixed and granulated to 105 corn starch paste. The resulting granulation is sieved, dried and blended with the remainder of the corn starch and the magnesium stearate. The resulting granulation is then compressed into tablets containing 1.0 mg, 25.0 mg, 26.0 mg, 50.0 mg and 100 mg of the active ingredient per tablet.

What is claimed is:

1. The compound represented by formula

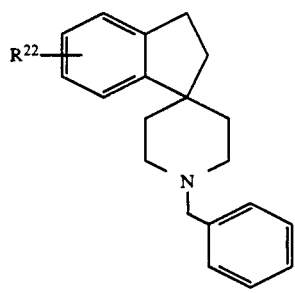

wherein R²² is selected from the group consisting of

C₁₋₆ alkyl, halogen, cyano, trifluoromethyl, nitro and hydroxy and pharmaceutically acceptable salts thereof.

2. The compound represented by formula IIB:

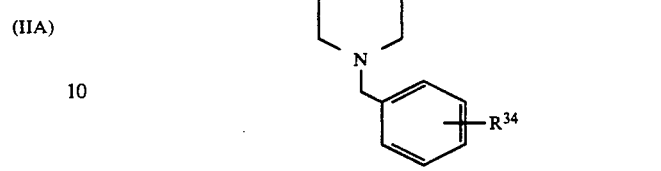

wherein R32 is selected from the group consisting of hydrogen, $C_{1-16}$ alkyl, halogen, cyano, trifluoromethyl, nitro, hydroxy and $C_{1-6}$ alkoxy; and R34 is selected from the group consisting of $C_{1-6}$ alkyl, halogen, cyano, trifluoromethyl, nitro, hydroxy and $C_{1-6}$ alkoxy and pharmaceutically acceptable salts thereof.

3. A compound according to claim 2 selected from:
1′-(4″-methylbenzyl)spiro[indane-1,4′-piperidine]; and
1′-(4″-methoxybenzyl)spiro[indane-1,4′-piperidine].

4. A pharmaceutical composition comprising an effective amount of a compound of formula IIA as defined in claim 1 or a pharmaceutically acceptable salt thereof in association with one or more pharmaceutically acceptable carriers and/or excipients.

5. A pharmaceutical composition comprising an effective amount of a compound of formula IIB as defined in claim 2 or a pharmaceutically acceptable salt thereof in association with one or more pharmaceutically acceptable carriers and/or excipients.

* * * * *